United States Patent [19]

Aoki et al.

[11] 4,351,897
[45] Sep. 28, 1982

[54] COLOR PHOTOGRAPHIC LIGHT-SENSITIVE MATERIAL

[75] Inventors: Kozo Aoki; Nobuo Seto; Yoshiharu Yabuki; Masakazu Morigaki; Nobuo Furutachi; Kotaro Nakamura, all of Minami-ashigara, Japan

[73] Assignee: Fuji Photo Film Co., Ltd., Kanagawa, Japan

[21] Appl. No.: 291,886

[22] Filed: Aug. 11, 1981

[30] Foreign Application Priority Data

Aug. 12, 1980 [JP] Japan ................................ 55-110943

[51] Int. Cl.³ .............................................. G03C 1/40
[52] U.S. Cl. .................................... 430/555; 430/504; 430/505; 430/544; 430/551
[58] Field of Search ............... 430/555, 505, 544, 382, 430/387, 504, 551

[56] References Cited

U.S. PATENT DOCUMENTS

| | | | |
|---|---|---|---|
| 3,148,062 | 9/1964 | Whitmore et al. | 430/382 |
| 3,227,554 | 1/1966 | Barr et al. | 430/555 |
| 3,615,506 | 10/1971 | Abbott et al. | 430/555 |
| 4,264,723 | 4/1981 | Ichijima et al. | 430/555 |
| 4,310,623 | 1/1982 | Watanabe et al. | 430/546 |

*Primary Examiner*—J. Travis Brown
*Attorney, Agent, or Firm*—Sughrue, Mion, Zinn, Macpeak & Seas

[57] ABSTRACT

A silver halide color photographic light-sensitive material is described comprising a support having thereon a photographic layer containing at least one coupler represented by formula (I) or (II)

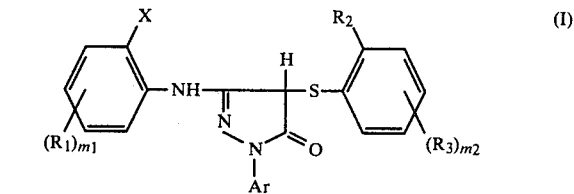

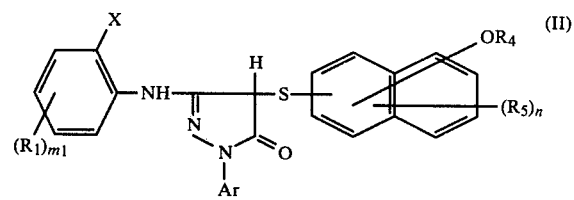

wherein Ar represents a phenyl group substituted with at least one substituent selected from a halogen atom, an alkyl group, an alkoxy group, an alkoxycarbonyl group and a cyano group; X represents a halogen atom or an alkoxy group; $R_1$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group, or a trifluoromethyl group; $R_2$ represents a halogen atom, a hydroxy group, an alkyl group, an alkoxy group or an aryl group; $R_3$ represents a hydrogen atom, a halogen atom, a hydroxy group, an alkyl group, an alkoxy group or an aryl group; at least one of $R_2$ and $R_3$ represents an alkoxy group; $m_1$ and $m_2$ each represents an integer from 1 to 4; $R_4$ represents an alkyl group or an aryl group; $R_5$ represents a hydrogen atom, a halogen atom, an alkyl group, an alkoxy group or an aryl group; n represents an integer from 1 to 6; and when $m_1$, $m_2$ and n each is 2 or more, each $R_1$, $R_3$ and $R_5$ may be the same or different.

The color photographic light-sensitive material containing a 2-equivalent magenta color image-forming coupler as described above has various advantages, for example, in that the dye formation efficiency in the color development step is high, the photographic properties are not influenced by variations in the pH of the color development bath, and the color images formed are fast to heat or light.

22 Claims, No Drawings

COLOR PHOTOGRAPHIC LIGHT-SENSITIVE MATERIAL

FIELD OF THE INVENTION

The present invention relates to a color photographic light-sensitive material, and more particularly to a color photographic light-sensitive material wherein the dye formation efficiency in the color development step is high, photographic properties are not influenced by variations in the pH of the color development bath, and the color images are fast to heat or light.

BACKGROUND OF THE INVENTION

Various pyrazolone derivatives have been known as magenta color image-forming couplers (referred to hereinafter simply as "magenta couplers"). However, these pyrazolone derivatives generally have low color formation efficiency (ratio of conversion of the coupler into a dye) when contained in photographic light-sensitive materials, and so-called 4-equivalent couplers, in which coupling position is not substituted, usually from only about ½ mol of dye per mol of the coupler.

To improve color formation efficiency, so-called 2-equivalent magenta couplers have been used, in which a substituent is introduced into the coupling position of a pyrazolone type magenta coupler, and the substituent splits off in the color development step. Examples of such couplers are disclosed, for example, in U.S. Pat. Nos. 3,331,476, 3,419,391, 3,617,291, and 3,926,631. Further, magenta couplers in which a substituent is linked to the coupling position through a sulfur ion are described in U.S. Pat. No. 3,214,437 (a thiocyano group), U.S. Pat. No. 4,032,346 (an acylthio group or a thioacylthio group), U.S. Pat. Nos. 3,227,554 and 3,701,783 and Japanese Patent Publication No. 34044/78 (an arylthio group or a heterocyclic thio group), and West German Patent Application (OLS) No. 2,944,601 (an alkylthio group).

It has been found as the result of the detailed investigations that when couplers having an arylthio group at the coupling active position among the magenta couplers described in U.S. Pat. Nos. 3,227,554 and 3,701,783 are used in a color photographic light-sensitive material and color images are formed, the light fastness of the color images does not completely satisfy the desired improvement in the properties of the color photographic light-sensitive materials.

Also, it has been found that when the magenta couplers which release an arylthio group as described in Japanese Patent Publication No. 34044/78 are used in a color photographic light-sensitive material and color images are formed, the light fastness of the color images is insufficient.

SUMMARY OF THE INVENTION

Therefore, a first object of this invention is to provide a color photographic light-sensitive material which forms color images which are fast to light.

A second object of this invention is to provide a color photographic light-sensitive material in which photographic properties are less influenced by variations in the pH of the color development bath.

A third object of this invention is to provide a color photographic light-sensitive material containing a low cost 2-equivalent magenta coupler by a simple production process.

A fourth object of this invention is to provide a color photographic light-sensitive material having improved color formation efficiency, reduced coupler content, and reduced silver halide content.

Other objects of this invention will become apparent from the following detailed description and examples.

The above-described objects of this invention can be effectively attained by incorporating a magenta coupler in which one hydrogen atom on the coupling position of the pyrazolone is substituted by an arylthio group in which at least one of the ortho positions is substituted or a naphthylthio group into a light-sensitive silver halide emulsion layer of a silver halide color photographic light-sensitive material.

More particularly, by using such a magenta coupler, which releases an ortho-substituted arylthio or a naphthylthio group, in a silver halide color photographic light-sensitive material, the following effects can be obtained:

(1) Color images obtained by coupling with an oxidation product of a color developing agent (for example, a p-phenylenediamine type developing agent) are remarkably fast to light or heat.

(2) Color formation efficiency of the magenta coupler is remarkably improved. Accordingly, the amount of magenta coupler used can be reduced as compared with prior art couplers and the amount of silver halide can also be significantly reduced. Consequently, it is possible to reduce the thickness of the magenta color image providing emulsion layer. As a result, the sharpness of images can be significantly improved.

(3) Color photographic light-sensitive materials can be produced at a moderate price by the reductions in the amount of coupler and the amount of silver halide used.

(4) The process of color development is stabilized (i.e., light-sensitive materials which are hardly influenced by variation of pH of photographic processing solutions can be obtained).

(5) A color photographic light-sensitive material having stabilized quality can be obtained, in which abnormal coloring during development does not occur when the material is allowed to stand in the presence of formaldehyde before development.

(6) Color photographic light-sensitive materials in which the granularity of color images after development is excellent can be obtained.

The magenta coupler which releases the arylthio group used in the present invention is represented by the following formula (I) or (II)

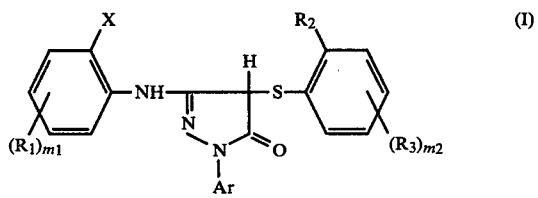

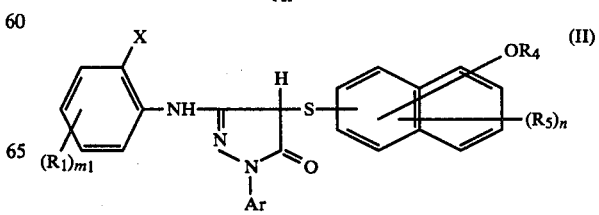

wherein Ar represents a phenyl group substituted with at least one substituent selected from a halogen atom, an alkyl group, an alkoxy group, an alkoxycarbonyl group and a cyano group; X represents a halogen atom or an alkoxy group; $R_1$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group or a trifluoromethyl group; $R_2$ represents a halogen atom, a hydroxy group, an alkyl group, an alkoxy group or an aryl group; $R_3$ represents a hydrogen atom, a halogen atom, a hydroxy group, an alkyl group, an alkoxy group or an aryl group; at least one of $R_2$ and $R_3$ represents an alkoxy group; $m_1$ and $m_2$ each represents an integer from 1 to 4; $R_4$ represents an alkyl group or an aryl group; $R_5$ represents a hydrogen atom, a halogen atom, an alkyl group, an alkoxy group or an aryl group; n represents an integer from 1 to 6; and when $m_1$, $m_2$ and n each is 2 or more, each $R_1$, $R_3$ and $R_5$ may be the same or different.

The magenta couplers which can be used in the color photographic light-sensitive material of the present invention are capable of drastically improving the light fastness of the color images. This fact cannot be expected from the conventionally known couplers releasing an arylthio group, and is very surprising, as will be apparent from the detailed description hereinafter.

DETAILED DESCRIPTION OF THE INVENTION

In formulae (I) and (II), Ar is a substituted phenyl group. The substituent for the phenyl group includes a halogen atom (for example, a chlorine atom, a bromine atom, a fluorine atom, etc.), an alkyl group having from 1 to 22 carbon atoms (for example, a methyl group, an ethyl group a tetradecyl group, a tert-butyl group, etc.), an alkoxy group having from 1 to 22 carbon atoms (for example, a methoxy group, an ethoxy group, an octyloxy group, a dodecyloxy group, etc.), an alkoxycarbonyl group having from 2 to 23 carbon atoms (for example, a methoxycarbonyl group, an ethoxycarbonyl group, a tetradecyloxycarbonyl group, etc.), or a cyano group.

X in formulae (I) and (II) represents a halogen atom (for example, a chlorine atom, a bromine atom, a fluorine atom, etc.) or an alkoxy group having from 1 to 22 carbon atoms (for example, a methoxy group, an octyloxy group, a dodecyloxy group, etc.).

$R_1$ in formulae (I) and (II) represents a hydrogen atom, a halogen atom (for example, a chlorine atom, a bromine atom, a fluorine atom, etc.), a straight chain or branched chain alkyl group (for example, a methyl group, a tert-butyl group, a tetradecyl group, etc.), an alkoxy group (for example, a methoxy group, an ethoxy group, a 2-ethylhexyloxy group, a tetradecyloxy group, etc.), an acylamino group (for example, an acetamido group, a benzamido group, a butanamido group, a tetradecanamido group, an α-(2,4-di-tert-amylphenoxy)acetamido group, an α-(2,4-di-tert-amylphenoxy)-butyramido group, an α-(3-pentadecylphenoxy)hexanamido group, an α-(4-hydroxy-3-tert-butylphenoxy)-tetradecanamido group, a 2-oxopyrrolidin-1-yl group, a 2-oxo-5-tetradecylpyrrolidin-1-yl group, an N-methyltetradecanamido group, etc.), a sulfonamido group (for example, a methanesulfonamido group, a benzenesulfonamido group, a p-toluenesulfonamido group, an octanesulfonamido group, a p-dodecylbenzenesulfonamido group, an N-methyltetradecanesulfonamido group, etc.), a sulfamoyl group (for example, an N-methylsulfamoyl group, an N-hexadecylsulfamoyl group, an N-[3-(dodecyloxy)propyl]sulfamoyl group, an N-[4-(2,4-di-tert-amylphenoxy)butyl]sulfamoyl group, an N-methyl-N-tetradecylsulfamoyl group, etc.), a carbamoyl group (for example, an N-methylcarbamoyl group, an N-octadecylcarbamoyl group, an N-[4-(2,4-di-tertamylphenoxy)butyl]carbamoyl group, an N-methyl-N-tetradecylcarbamoyl group, etc.), a diacylamino group (for example, an N-succinimido group, an N-phthalimido group, a 2,5-dioxo-1-oxazolidinyl group, a 3-dodecyl-2,5-dioxo-1-hydantoinyl group, a 3-(N-acetyl-N-dodecylamino)succinimido group, etc.), an alkoxycarbonyl group (for example, a methoxycarbonyl group, a tetradecyloxycarbonyl group, a benzyloxycarbonyl group, etc.), an alkoxysulfonyl group (for example, a methoxysulfonyl group, an octyloxysulfonyl group, a tetradecyloxysulfonyl group, etc.), an aryloxysulfonyl group (for example, a phenoxysulfonyl group, a 2,4-di-tert-amylphenoxysulfonyl group, etc.), an alkanesulfonyl group (for example, a methanesulfonyl group, an octanesulfonyl group, a 2-ethylhexanesulfonyl group, a hexadecanesulfonyl group, etc.), an arylsulfonyl group (for example, a benzenesulfonyl group, a 4-nonylbenzenesulfonyl group, etc.), an alkylthio group (for example, an ethylthio group, a hexylthio group, a benzylthio group, a tetradecylthio group, a 2-(2,4-di-tert-amylphenoxy)ethylthio group, etc.), an arylthio group (for example, a phenylthio group, a p-tolylthio group, etc.), an alkyloxycarbonylamino group (for example, an ethyloxycarbonylamino group, a benzyloxycarbonylamino group, a hexadecyloxycarbonylamino group, etc.), an alkylureido group (for example, an N-methylureido group, an N,N-dimethylureido group, an N-methyl-N-dodecylureido group, an N-hexadecylureido group, an N,N-dioctadecylureido group, etc.), an acyl group (for example, an acetyl group, a benzoyl group, an octadecanoyl group, a p-dodecanamidobenzoyl group, etc.), a nitro group, a carboxy group or a trichloromethyl group. In the above-described substituents, the alkyl moieties thereof preferably have from 1 to 36 carbon atoms, and the aryl moieties thereof preferably have from 6 to 38 carbon atoms.

$R_2$ in formula (I) represents a halogen atom (for example, a chlorine atom, a bromine atom, a fluorine atom, etc.), a hydroxy group, an alkyl group having from 1 to 22 carbon atoms (for example, a methyl group, an ethyl group, a tert-butyl group, a 1,1,3,3-tetramethylbutyl group, a 2-(2,4-di-tert-amylphenoxy)ethyl group, etc.), an alkoxy group having from 1 to 22 carbon atoms (for example, a methoxy group, a butoxy group, an octyloxy group, a dodecyloxy group, a hexadecyloxy group, a 2-dodecyloxyethoxy group, etc.) or an aryl group (for example, a phenyl group, an α- or β-naphthyl group, a p-tolyl group, etc.).

$R_3$ in formula (I) represents a hydrogen atom, a hydroxy group, or a halogen atom, an alkyl group, an alkoxy group, or an aryl group, each as defined for $R_2$ above. At least one of $R_2$ and $R_3$ is an alkoxy group.

$R_4$ in formula (II) represents an alkyl group having from 1 to 22 carbon atoms (for example, a methyl group, a propyl group, a 2-ethylhexyl group, a dodecyl group, a hexadecyl group, a 2-(2,4-di-tert-amylphenoxy)ethyl group, a 2-dodecyloxyethyl group, etc.) or an aryl group (for example, a phenyl group, an α- or β-naphthyl group, a 4-tolyl group, etc.).

$R_5$ in formula (II) represents a hydrogen atom, a halogen atom (for example, a chlorine atom, a bromine atom, a fluorine atom, etc.), an alkyl group having from 1 to 22 carbon atoms (for example, a methyl group, an ethyl group, a tert-butyl group, a benzyl group, a 2-(2,4-di-tert-amylphenoxy)ethyl group, a tetradecyl group, etc.), an alkoxy group having from 1 to 22 carbon atoms (for example, a methoxy group, a 2-ethylhexyloxy group, an octyloxy group, a 2-dodecyloxyethoxy group, a hexadecyloxy group, etc.) or an aryl group (for example, a phenyl group, an α- or β-naphthyl group, a p-tolyl group, etc.).

Of the couplers represented by formulae (I) and (II), those in which the total number of carbon atoms included in the groups represented by $R_2$ and $R_3$ is at least 6, and those in which the total number of carbon atoms included in the groups represented by $R_4$ and $R_5$ is at least 4, are particularly preferred for achieving the objects of the present invention.

Specific examples of the typical couplers according to this invention are set forth below, but the present invention is not to be construed as being limited to these compounds.

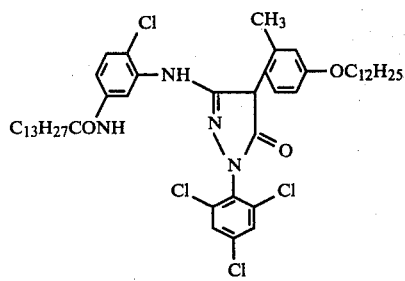
(1)

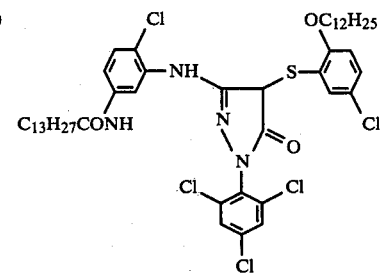
(2)

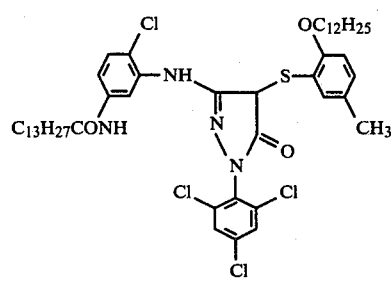
(3)

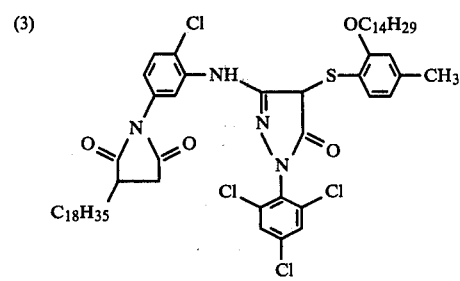
(4)

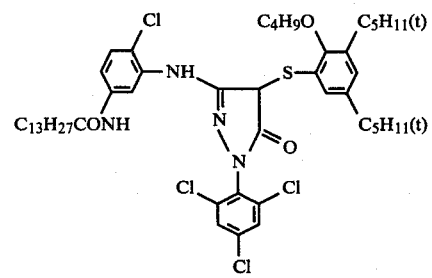
(5)

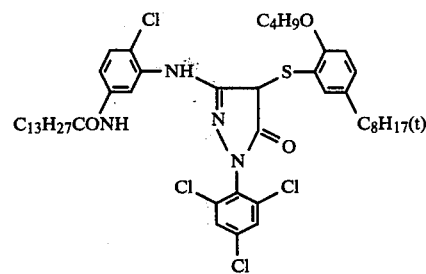
(6)

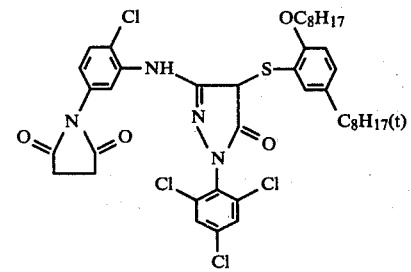
(7)

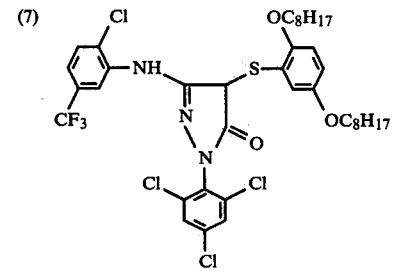
(8)

-continued

-continued
(19) 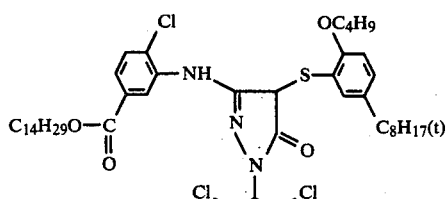
(20) 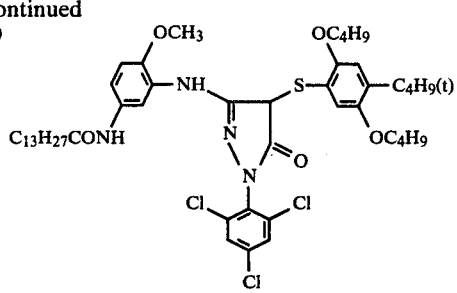
(21) 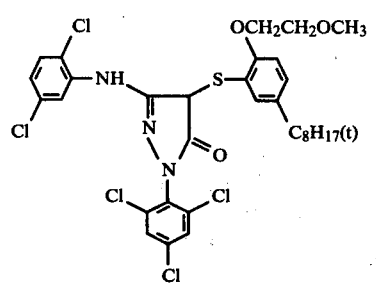
(22) 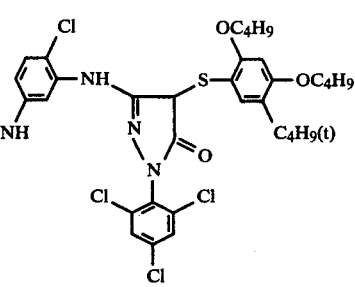
(23) 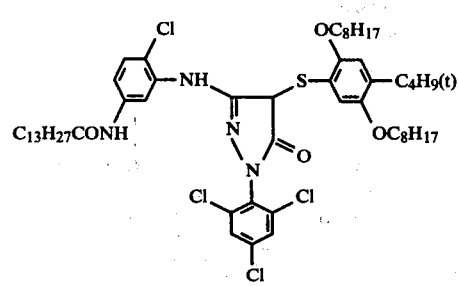
(24) 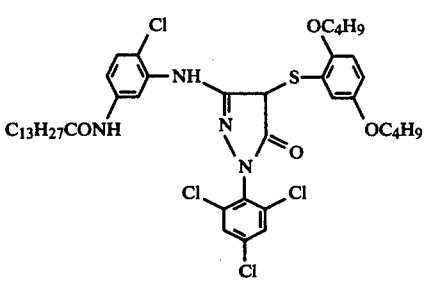
(25) 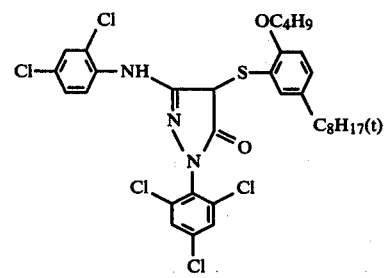
(26) 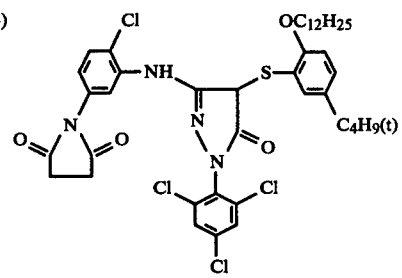
(27) 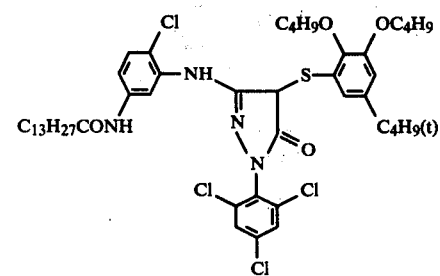
(28) 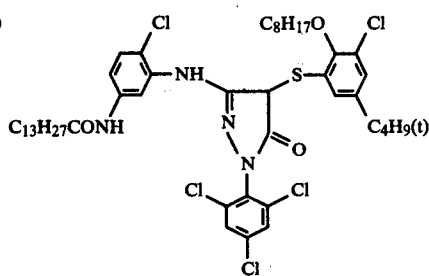
(29) 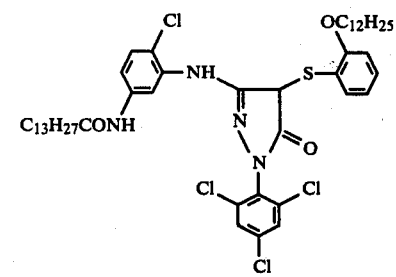
(30) 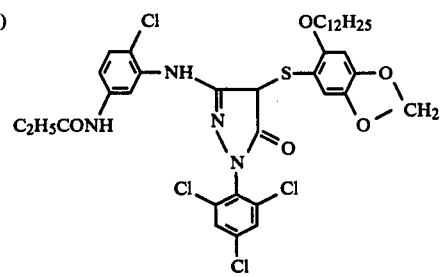

-continued
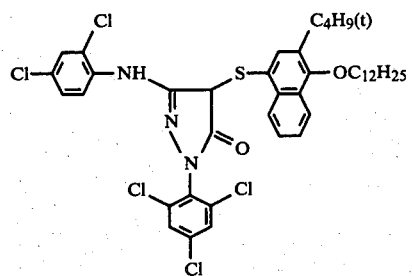 (31)
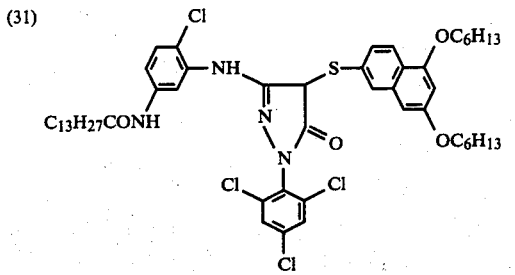 (32)
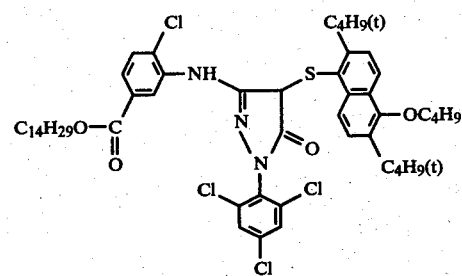 (33)
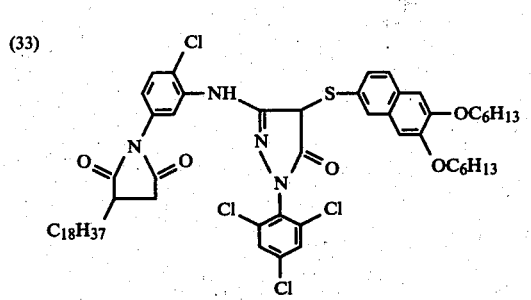 (34)
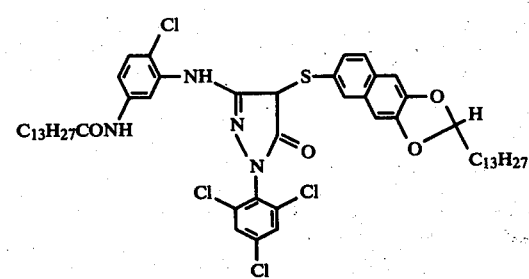 (35)
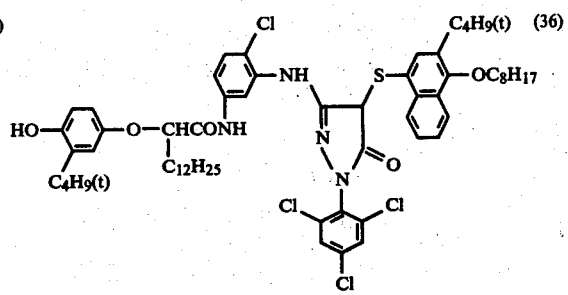 (36)
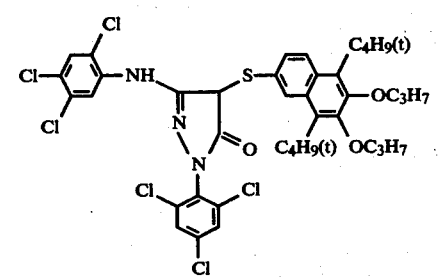 (37)
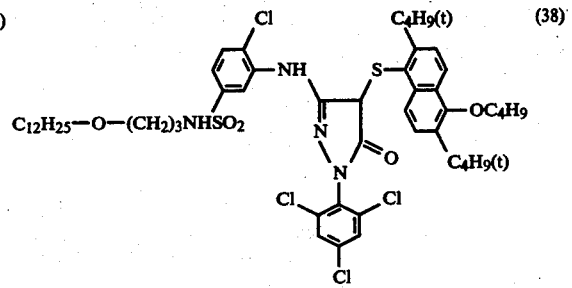 (38)
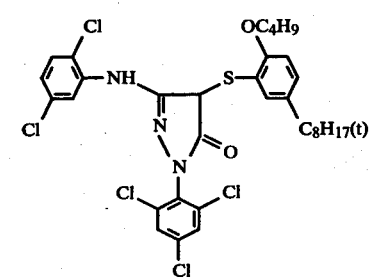 (39)
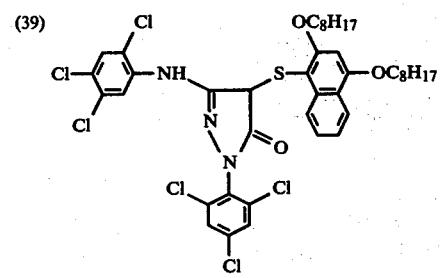 (40)

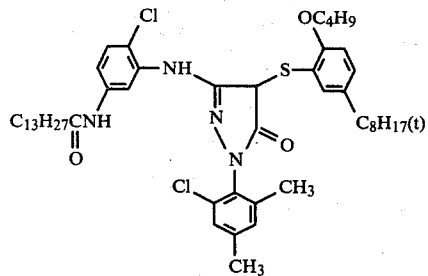 (41)

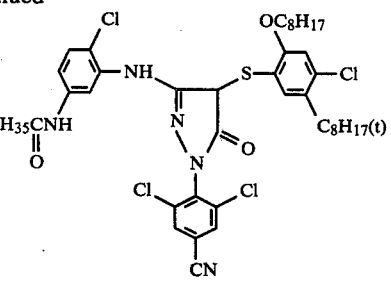 (42)

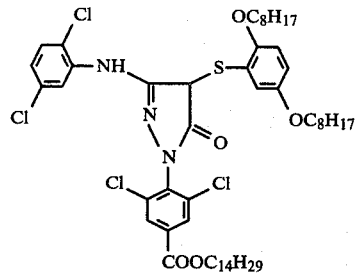 (43)

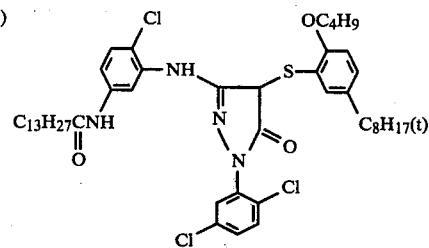 (44)

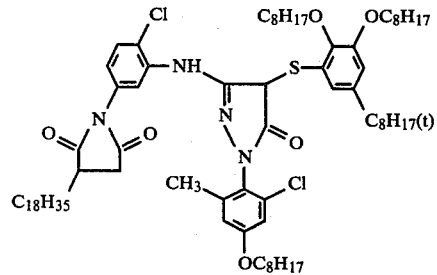 (45)

The couplers used in the present invention can by synthesized from thiophenol derivative which corresponds to the desired coupling releasable group and a so-called 4-equivalent couplers, in which the coupling active position is unsubstituted, according to the following methods.

1. A thiophenol derivative or a corresponding disulfide is converted into a sulphenyl halide by treatment with a halogenating agent (for example, chlorine, bromine, sulfuryl chloride, N-bromosuccinimide, etc.), and then the sulphenyl halide is reacted with a 4-equivalent coupler in the presence of a basic catalyst, or in the absence of a catalyst, to introduce an arylthio group to the coupling active position of the coupler as set forth in Reaction Scheme I below. This method can also be conducted by the addition of a halogen (i.e., halogen in a form of gas or liquid) in a mixture of a thiophenol derivative and a 4-equivalent coupler. This method is described in U.S. Pat. No. 3,227,554.

Reaction Scheme I

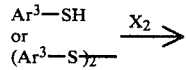

$Ar^3$—SH
or
$(Ar^3$—S$)_2$ $\xrightarrow{X_2}$

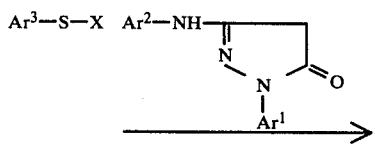

-continued
Reaction Scheme I

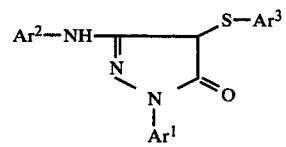

wherein $Ar^2$ represents a group of

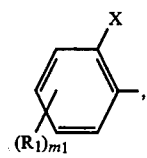, and $Ar^3$ represents a group of

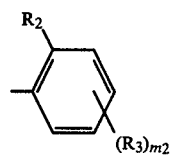

or a group of

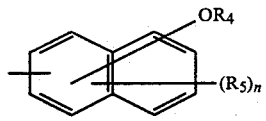

where X, $R_1$, $R_2$, $R_3$, $R_4$, $R_5$, $m_1$, $m_2$ and n are the same as defined in the formulae (I) and (II).

2. After the amino group of a 4-equivalent coupler is protected by acylation (for example, an acetyl group, an ethoxycarbonyl group, etc.), the active position thereof is treated with a halogenating agent and the resulting halogen substituted compound is reacted with a thiophenol derivative in the presence of a basic catalyst, or in the absence of a catalyst, to introduce the arylthio group to the coupling active position of the coupler. By removing the protective group, the desired 2-equivalent coupler is obtained, as set forth in Reaction Scheme II below. This method can be carried out in the manner similar to the method described in Japanese Patent Application (OPI) No. 91862/77 (the term "OPI" as used herein refers to a "published unexamined Japanese patent application").

Reaction Scheme II

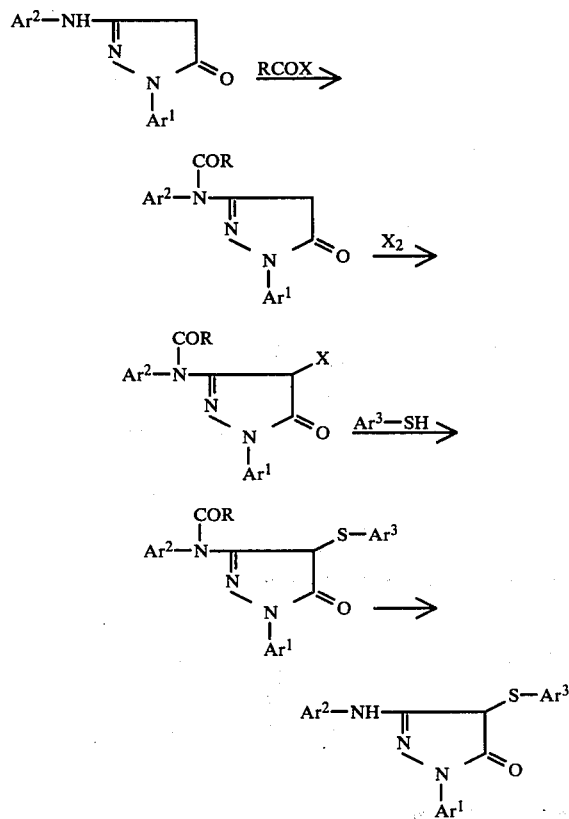

The thiophenol derivative or the corresponding disulfide, which is the source of the coupling releasable group, can be synthesized according to the following methods.

3. A corresponding aniline derivative is reacted with sodium nitrite under an acidic condition to form the diazonium salt, and then the latter is reacted with sodium sulfide or sodium disulfide to obtain a thiophenol derivative or a corresponding disulfide, respectively, as set forth in Reaction Scheme III below. This method is described in S. R. Sandler, W. Karo, *Organic Functional Group Preparations*, pp. 480–485, Academic Press (1968).

Reaction Scheme III

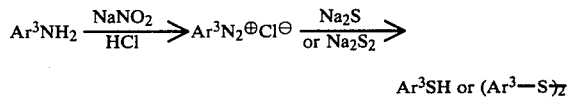

4. A benzene derivative including a substituent suited for the purpose of this invention is chlorosulfonated with chlorosulfonic acid, and then the resulting compound is reduced using metallic zinc or metallic tin and an acid, to obtain a thiophenol derivative as set forth in Reaction Scheme IV below. This method is described in S. R. Sandler, W. Karo, *Organic Functional Group Preparations*, pp. 480–485, Academic Press (1968).

Reaction Scheme IV

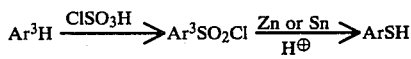

This method is applicable to a sulfonyl chloride which is produced by reaction of a corresponding sulfonic acid with thionyl chloride, phosphorus oxychloride, etc., when an appropriate sulfonic acid is available as a starting material. Also, it is possible to obtain a corresponding disulfide using hydrogen iodide as a reducing agent.

5. After converting a corresponding phenol derivative to a sodium salt, the latter is reacted with dimethylthiocarbamoyl chloride to form a dimethylthionecarbamate, and the resulting compound is subjected to heat rearrangement and hydrolysis through a dimethylthiolcarbamate to obtain a thiophenol derivative as set forth in Reaction Scheme V below. This method is described in *J. Org. Chem.*, Vol. 31, p. 3980 (1956).

Reaction Scheme V

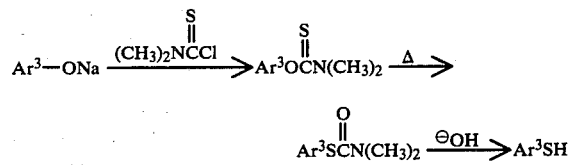

Synthesis examples of typical compounds according to this invention are set forth below, but other couplers can be synthesized by the combination of the synthesis methods generally described below.

SYNTHESIS EXAMPLE 1

Synthesis of 1-(2,4,6-trichlorophenyl)-4-(5-chloro-2-dodecyloxy-phenylthio)-3-(2-chloro-5-tetradecanamidoanilino)-2-pyrazolin-5-one [Coupler (2)]

(i) Synthesis of 5-chloro-2-dodecyloxythiophenol

A mixture of 28.3 g of p-chlorophenol, 52.5 g of tetradecyl bromide and 50 g of potassium carbonate was heated in 150 ml of acetone for 20 hours with stirring. After cooling, the reaction mixture was poured into ice water. The crystals thus-deposited were collected by filtration, washed with water, washed with methanol and dried to obtain 54.8 g of the crystals.

29.7 g of the above-described crystals was dissolved in 120 ml of chloroform and to the solution was added dropwise 20 ml of chlorosulfonic acid under cooling with ice. After stirring for 2 hours at room temperature, the reaction mixture was poured into ice water. The organic layer was separated, washed with an aqueous saturated sodium chloride solution and chloroform was distilled off under reduced pressure. To the residue were added 180 g of ice water, 35 ml of surfuric acid, and 31.2 g of zinc powder, and the mixture was stirred at 80° C. for 2 hours. After cooling, the residual zinc was removed by filtration and the mixture was extracted with ethyl acetate. The extract was washed with an aqueous saturated sodium chloride solution and ethyl acetate was distilled off under reduced pressure. The residue was separated through a column with a silica gel (using hexane as a spreading agent) to obtain 25 g of the oily desired product.

(ii) Synthesis of Coupler (2)

15 g of 5-chloro-2-dodecyloxythiophenol was dissolved in 40 ml of methylene chloride, and to the solution was added dropwise 4.2 ml of sulfuryl chloride. After stirring at room temperature for 45 minutes, the solvent was distilled off to obtain red colored oily sulphenyl chloride.

25 g of 1-(2,4,6-trichlorophenyl)-3-(2-chloro-5-tetradecanamidoanilino)-2-pyrazolin-5-one was dissolved in 100 ml of methylene chloride and to the solution was added 17.5 g of triethylamine. To the resulting mixture was added a solution of the sulphenyl chloride obtained above dissolved in 20 ml of methylene chloride. After stirring at 40° C. for 2 hours, the solvent was distilled off under reduced pressure, and the residue was dissolved in a warm mixture of ethyl acetate and ethanol. The solution was washed with diluted acetic acid, and then with aqueous saturated sodium chloride, and then the solvent was distilled off under reduced pressure. The residue was recrystallized twice from a mixture of ethyl acetate and acetonitrile, to obtain 27 g of the desired coupler. The melting point was 160° to 161° C.

Elemental Analysis: Calculated: C: 59.97%, H: 6.75%, N: 5.95%, Found: C: 59.74%, H: 6.70%, N: 5.93%.

SYNTHESIS EXAMPLE 2

Synthesis of 1-(2,4,6-trichlorophenyl)-3-(2-chloro-5-tetradecanamidoanilino)-4-(2,5-di-tert-hexyl-4-methoxyphenylthio)-2-pyrazolin-5-one [Coupler (16) described above]

(i) Synthesis of 2,5-di-tert-hexyl-4-methoxythiophenol 50 g of 2,5-di-tert-hexyl-4-methoxyphenol was dissolved in 500 ml of toluene, and to the solution was added 11 g of potassium hydroxide. After removing water under refluxing by heating, to the residue was added dropwise melted dimethylthiocarbamoyl chloride. After stirring with heating for 2 hours, the toluene was distilled off and the residue was poured into water. The mixture was extracted with ethyl acetate, washed with water, and the ethyl acetate solvent was distilled off under reduced pressure. The residue was dissolved in 30 ml of sulfolane (i.e., tetrahydro-1,1-dioxidethiophene) and the solution was heated at 275° C. for 1 hour while stirring. After cooling, ethyl acetate was added to the mixture, the mixture was washed with water, and the solvent was distilled off under reduced pressure. To the residue were added 200 ml of methanol and 20 g of potassium hydroxide, and the mixture was refluxed for 2 hours by heating. After cooling, the mixture was acidified with hydrochloric acid and extracted with ethyl acetate. After washing with water, the solvent was distilled off under reduced pressure and the residue was crystallized from methanol to obtain 12.5 g of the desired compound.

(ii) Synthesis of Coupler (16)

24 g of the desired coupler was obtained in an analogous manner to that described in step (ii) of Synthesis Example 1, using 12.5 g of 2,5-di-tert-hexyl-4-methoxythiophenol and 22 g of 1-(2,4,6-trichlorophenyl)-3-(2-chloro-5-tetradecanamidoanilino)-2-pyrazolin-5-one. The melting point was 183° to 185° C.

Elemental Analysis: Calculated: C: 62.60%, H: 7.22%, N: 6.08%, Found: C: 62.64%, H: 7.38%, N: 6.10%.

The magenta coupler of the formula (I) or (II) is coated in an amount of about $2 \times 10^{-3}$ mol to about $5 \times 10^{-1}$ mol, preferably $1 \times 10^{-2}$ mol to $5 \times 10^{-1}$ mol, per mol of silver.

The photographic emulsion layer of a photographic light-sensitive material according to this invention can contain other color-forming couplers, that is, a compound capable of forming a dye upon oxidative coupling with an aromatic primary amine developing agent (for example, a phenylenediamine derivative, an aminophenol derivative, etc.) in color development processing, in addition to a coupler according to the present invention. For instance, a 5-pyrazolone coupler, a pyrazolobenzimidazole coupler, a cyanoacetyl chroman coupler and an open-chain acylacetonitrile coupler can be used as a magenta-dye-forming coupler; an acylacetamide coupler (for example, a benzoyl acetanilide, pivaloyl acetanilide, etc.) can be used as a yellow coupler; and a naphthol coupler and a phenol coupler can be used as a cyan-dye-forming coupler. A non-diffusible coupler which contains a hydrophobic group, called a ballast group, in the molecule thereof is preferred as a coupler. These couplers can be 4-equivalent or 2-equivalent. In addition, a colored coupler providing a color correction effect, or a coupler which releases a development inhibitor upon development (a so-called DIR coupler) can also be present therein. Also, in addition to a DIR coupler, a colorless DIR coupling compound which provides a colorless product upon the coupling reaction and releases a development inhibitor can be present in the photographic light-sensitive material.

Specific examples of the magenta color-forming couplers which can be employed are those described, for example, in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76 and 55122/78, and so forth.

Specific examples of the yellow color-forming couplers which can be employed are those described, for example, in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77, and so forth.

Specific examples of the cyan color-forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830 and 2,454,329, Japanese Patent Application (OPI) Nos. 59838/73, 26034/76, 5055/73, 146828/76, 69624/77 and 90932/77, and so forth.

Specific examples of the colored couplers which can be employed are those described, for example, in U.S. Pat. Nos. 3,476,560, 2,521,908 and 3,034,892, Japanese Patent Publication Nos. 2016/69, 22335/63, 11304/67, and 32461/69, Japanese Patent Application (OPI) Nos. 26034/76 and 42121/77, West German Patent Application (OLS) No. 2,418,959, and so forth.

Specific examples of DIR couplers which can be employed are those described, for example, in U.S. Pat. Nos. 3,227,554, 3,617,291, 3,701,783, 3,790,384 and 3,632,345, West German Patent Application (OLS) Nos. 2,414,006, 2,454,301 and 2,454,329, British Pat. No. 953,454, Japanese Patent Application Nos. 69624/77, 122335/74, Japanese Patent Publication No. 16141/76, and so forth.

As noted above, in addition to a DIR coupler, other compounds which release a development inhibitor upon development can also be present in the light-sensitive material. For example, DIR compounds as described, for example, in U.S. Pat. Nos. 3,297,445 and 3,379,529, West German Patent Application (OLS) No. 2,417,914, Japanese Patent Application (OPI) Nos. 15271/77 and 9116/78, etc., can be employed.

Known methods, for example, the method described in U.S. Pat. No. 2,322,027, can be employed to incorporate the coupler into the silver halide emulsion layer. For example, the coupler can be dissolved in a phthalic acid alkyl ester (e.g., dibutyl phthalate, dioctyl phthalate, etc.), a phosphoric acid ester (e.g., diphenyl phosphate, triphenyl phosphate, tricresyl phosphate, dioctylbutyl phosphate, etc.), a citric acid ester (e.g., tributyl acetylcitrate, etc.), a benzoic acid ester (e.g., octyl benzoate, etc.), an alkyl amide (e.g., diethyl laurylamide, etc.), a fatty acid ester (e.g., dibutoxyethyl succinate, dioctyl azelate, etc.), a trimesic acid ester (e.g., tributyl trimesate, etc.), etc.; or an organic solvent having a boiling point of from about 30° to 150° C. such as a lower alkyl acetate (e.g., ethyl acetate, butyl acetate, etc.), ethyl propionate, sec-butyl alcohol, methyl isobutyl ketone, β-ethoxyethyl acetate, methyl cellosolve acetate, etc. Then the solution is dispersed in a hydrophilic colloid. The above-described organic solvents having a high boiling point and the above-described organic solvents having a low boiling point may be used as mixtures, if desired.

Furthermore, the dispersing method using a polymeric material as described in Japanese Patent Publication No. 39853/76, Japanese Patent Application (OPI) No. 59943/76 can also be used.

When a coupler having an acid group, such as a carboxylic acid group, a sulfonic acid group, etc., is used, it can be incorporated in a hydrophilic colloid as an alkaline aqueous solution thereof.

The photographic light-sensitive material prepared according to the present invention can also contain, as a color fog preventing agent, a hydroquinone derivative, an aminophenol derivative, a gallic acid derivative, an ascorbic acid derivative, or the like. Specific examples of these agents are described in U.S. Pat. Nos. 2,360,290, 2,336,327, 2,403,721, 2,418,613, 2,675,314, 2,701,197, 2,704,713, 2,728,659, 2,732,300 and 2,735,365, Japanese Patent Application (OPI) Nos. 92988/75, 92989/75, 93928/75, 110337/75 and 146235/77, Japanese Patent Publication No. 23813/75, and so forth.

The hydrophilic colloid layers of the photographic light-sensitive material prepared in accordance with the present invention can also contain an UV absorbent. For example, a benzotriazole compound substituted with an aryl group, a 4-thiazolidone compound, a benzophenone compound, a cinnamic acid ester compound, butadiene compound, a benzoxazole compound, an UV absorbing polymer, etc., can be employed. These UV absorbents may be fixed in the above-described hydrophilic colloid layer, if desired.

Specific examples of UV absorbents which can be employed are those described, for example, in U.S. Pat. Nos. 3,533,794, 3,314,794 and 3,352,681, Japanese Patent Application (OPI) No. 2784/71, U.S. Pat. Nos. 3,705,805, 3,707,375, 4,045,229, 3,700,455 and 3,499,762, West German Patent Publication No. 1,547,863, and so forth.

In the practice of the present invention, known color fading preventing agents as described below can be employed. The color fading preventing agent can be used individually or in a combination of two or more thereof. Known color fading preventing agents include a hydroquinone derivatives, gallic acid derivatives, p-alkoxyphenols, p-oxyphenol derivatives, and bisphenols, etc.

Specific examples of the hydroquinone derivatives are described, for example, in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921, etc. Specific examples of the gallic acid derivatives are described, for example, in U.S. Pat. Nos. 3,457,079 and 3,069,262, etc. Specific examples of the p-alkoxyphenols are described, for example, in U.S. Pat. Nos. 2,735,765 and 3,698,909, Japanese Patent Publication Nos. 20977/74 and 6623/77, etc. Specific examples of the p-oxyphenol derivatives are described, for example, in U.S. Pat. Nos. 3,432,300, 3,573,050, 3,574,627 and 3,764,337, Japanese Patent Application (OPI) Nos. 35633/77, 147434/77 and 152225/77, etc. Specific examples of the bisphenols are described, for example, in U.S. Pat. No. 3,700,455, etc.

In the photographic light-sensitive material prepared in accordance with the present invention, the photographic emulsion layer and other hydrophilic colloid layers may contain therein a dispersion of a water-insoluble or water-sparingly-soluble synthetic polymer for the purposes of improving dimensional stability and so forth. Synthetic polymers which can be used include a polymer derived from a monomer unit comprising an alkyl acrylate or methacrylate, an alkoxyalkyl acrylate or methacrylate, a glycidyl acrylate or methacrylate, an acrylamide, a methacrylamide, a vinyl ester (e.g., vinyl acetate), acrylonitrile, an olefin, styrene, etc., individually or in a combination thereof, and a copolymer derived from a monomer unit as described above and a monomer unit comprising acrylic acid, methacrylic acid, an α,β-unsaturated dicarboxylic acid, a hydroxyalkyl acrylate or methacrylate, a sulfoalkyl acrylate or methacrylate, styrenesulfonic acid, etc.

The photographic emulsion layer and other hydrophilic colloid layer of the photographic light-sensitive material prepared in accordance with the present invention can contain a whitening agent, such as a stilbene, a triazine, an oxazole, or a coumarin, etc. These agents can be water-soluble, or can be employed as a dispersion of the water-insoluble whitening agent. Specific examples of fluorescent whitening agents are described in U.S. Pat. Nos. 2,632,701, 3,269,840 and 3,359,102, and British Pat. Nos. 852,075 and 1,319,763, *Research Disclosure*, Vol. 176, No. 17643, p. 24, left-side column, ll. 9–36, "Brighteners", (December, 1978).

In photographic processing of the photographic light-sensitive material prepared in accordance with the present invention, any known methods can be used. Known processing solutions can be used. The processing temperature is usually selected within the range of from 18° C. to 50° C. However, temperatures lower than 18° C. and temperatures higher than 50° C. can be employed, if desired. According to the particular purpose, either a development processing for forming a silver image (black-and-white photographic processing) or a color photographic processing comprising a development processing for forming a dye image can be used.

As a fixing solution, a solution having a composition generally used can be used. A fixing agent which can be used includes a thiosulfuric acid salt and a thiocyanic acid salt. Additionally, an organic sulfur compound which is known to have the effect as a fixing agent can be used. The fixing solution may contain therein a water-soluble aluminum salt as a hardener.

Conventional methods can be employed for forming a dye image. Among methods that can be employed are: (1) a negative-positive method, for example, as described in *Journal of the Society of Motion Picture and Television Engineers*, Vol. 61, pp. 667–701 (1953); (2) a color reversal method which comprises developing with a developer containing a black-and-white developing agent to form a negative silver image, then subjecting the photographic material to at least one uniform exposure or to another appropriate fogging treatment, and subsequently performing color development to obtain positive dye images; and (3) a silver dye bleaching method which comprises exposing a dye-containing photographic emulsion layer and developing the same to form a silver image and then bleaching the dyes using the silver image as a bleaching catalyst.

The color developer generally comprises an alkaline aqueous solution containing a color developing agent. Suitable color developing agent which can be employed includes a known primary aromatic amine developing agent, e.g., a phenylenediamine (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfamidoethylaniline, 4-amino-3-methyl-N-ethyl-N-β-methoxyethylaniline, etc.).

In addition, a developing agent described in L. F. A. Mason, *Photographic Processing Chemistry*, at pages 226 to 229, Focal Press (1966), U.S. Pat. Nos. 2,193,015 and 2,592,364, Japanese Patent Application (OPI) No. 64933/73, etc., can be employed.

The color developer can also contain a pH buffering agent, such as a sulfite, a carbonate, a borate, or a phosphate of an alkali metal, a developing inhibitor or an anti-fogging agent such as a bromide, an iodide, an organic anti-fogging agent, etc. In addition, if desired, the color developer can also contain a water softener; a preservative such as hydroxylamine; an organic solvent such as benzyl alcohol, diethylene glycol, etc.; a developing accelerator such as polyethylene glycol, a quaternary ammonium salt, an amine; a dye-forming coupler; a competing coupler; a fogging agent such as sodium borohydride; an auxiliary developer such as 1-phenyl-3-pyrazolidone; a viscosity-imparting agent; a polycarboxylic acid type chelating agent described in U.S. Pat. No. 4,083,723; and anti-oxidizing agent as described in West German Patent Application (OLS) No. 2,622,950; and the like.

The photographic emulsion after color development are generally bleach-processed. Bleach processing can be performed at the same time as fixing, or separately therefrom. Suitable bleaching agents which can be employed include a compound of a polyvalent metal such as iron (III), cobalt (IV), chromium (VI), copper (II), etc., a peracid, a quinone, a nitroso compound, etc. Specific examples include a ferricyanide; a bichromate; an organic complex of iron (III) or cobalt (IV); an aminopolycarboxylic acid such as ethylenediaminetetraacetic acid, nitrilotriacetic acid, 1,3-diamino-2-propanol tetraacetic acid, etc.; a complex of an organic acid such as citric acid, tartaric acid, malic acid, etc.; a persulfate; a permanganate; nitrosophenol; etc. Of these, a particularly useful bleaching agent is potassium ferricyanide, sodium ethylenediaminetetraacetate iron (III), or ammonium ethylenediaminetetraacetate iron (III). Ethylenediaminetetraacetate iron (III) complex is useful both in a bleaching solution and in a monobath bleach-fixing solution.

A bleaching and bleach-fixing solution can contain various additives, including a bleach accelerating agent as described in U.S. Pat. Nos. 3,042,520 and 3,241,966, Japanese Patent Publication Nos. 8506/70 and 8836/70, a thiol compound as described in Japanese Patent Application (OPI) No. 65732/78, and the like.

The photographic light-sensitive material prepared using the present invention may be subjected to processing with a developing solution which is replenished or otherwise maintains its properties by the methods as described in Japanese Patent Application (OPI) Nos. 84636/76, 119934/77, 46732/78, 9626/79, 19741/79 and 37731/79.

The photographic light-sensitive material prepared using the present invention may be processed with a bleach-fixing solution which can be subjected to regeneration treatment, such as by methods as described in Japanese Patent Application (OPI) Nos. 781/71, 49437/73, 18191/73, 145231/75, 18541/76, 19535/76 and 144620/76, Japanese Patent Publication No. 23178/76, etc.

The present invention is illustrated in greater detail by reference to the following examples which, however, are not to be construed as limiting the invention.

EXAMPLE 1

10 g of Cp-A (a magenta coupler illustrated in Table 1) was dissolved in a mixture of 20 ml of tricresyl phosphate and 20 ml of ethyl acetate, and the resulting solution was dispersed in 80 g of a 10% aqueous gelatin solution containing sodium dodecylbenzenesulfonate to obtain an emulsified dispersion. Then, this emulsified dispersion was mixed with 150 g of a green-sensitive silver chlorobromide emulsion (bromide: 50 mol%) (containing 8.8 g of silver), sodium dodecylbenzenesulfonate was added as a coating aid and it was coated on a paper support both sides of which were laminated with polyethylene. Further, on this layer, a gelatin coating solution was coated (gelatin 1 g/m$^2$) as a protective layer, and dried to prepare Sample 1.

Samples 2 to 14 were prepared in the same manner as described above, except for changing the amount of the green-sensitive silver chlorobromide emulsion added to 75 g, and changing the coupler and amount thereof to those set forth in Table 1 below.

These samples were exposed to light at 1,000 lux/sec using a sensitometer, and then processed in the following processing solutions.

| Color Developer Solution | |
|---|---|
| Benzyl Alcohol | 15 ml |
| Sodium Sulfite | 5 g |
| Potassium Bromide | 0.4 g |
| Hydroxylamine Sulfate | 2 g |
| 4-Amino-3-methyl-N—ethyl-N—[β-(methanesulfonamido)ethyl]-p-phenylenediamine | 6 g |

| -continued | |
|---|---|
| Sodium Carbonate Monohydrate | 30 g |
| Water to make | 1,000 ml |
| | (pH 10.1) |
| Bleach-Fixing Solution | |
| Ammonium Thiosulfate (70% aq. soln.) | 150 ml |
| Sodium Sulfite | 15 g |
| Sodium Ferric Ethylenediamine-tetraacetate | 40 g |
| Ethylenediaminetetraacetic Acid | 4 g |
| Water to make | 1,000 ml |
| | (pH 6.9) |

| Processing Step | Temperature (°C.) | Time |
|---|---|---|
| Color Development | 33 | 3 min 30 sec |
| Bleach-Fixing | 33 | 1 min 30 sec |
| Washing | 28 to 35 | 3 min |

Each of these samples in which dye images had been thus formed was subjected to a fading test for 5 days using a Xenon fading tester (200,000 lux) equipped with an ultraviolet light-absorbing filter, absorbing light of a wavelength of 400 nm or shorter (manufactured by Fuji Photo Film Co., Ltd.). The measurement of the optical density of the color image and color stain was carried out using a Macbeth Densitometer with a Status AA filter. The results of the measurement are shown in Table 2 below.

TABLE 1

| Sample No. | Structure of Coupler | Coupler No. | Amount of Coupler Added | Coated Amount of Silver / Coated Amount of Coupler (mg/m$^2$ / mg/m$^2$) | Remarks |
|---|---|---|---|---|---|
| 1 | [structure: C$_{13}$H$_{27}$CONH-phenyl(Cl)-NH-pyrazolone-N-(2,4,6-trichlorophenyl)] | Cp-A | 10.0 g | 330/375 | Comparison |
| 2 | [structure: (t)C$_4$H$_9$-phenyl-OCH(C$_2$H$_5$)CONH-pyrazolone with S-phenyl(COOC$_2$H$_5$) and N-phenyl-O-phenyl-C$_4$H$_9$(t)] | Cp-B | 11.7 g | 165/440 | Comparison |
| 3 | [structure: C$_{13}$H$_{27}$CONH-phenyl(Cl)-NH-pyrazolone with S-phenyl(COOC$_2$H$_5$) and N-(2,4,6-trichlorophenyl)] | Cp-C | 12.9 g | 165/484 | Comparison |

TABLE 1-continued

| Sample No. | Structure of Coupler | Coupler No. | Amount of Coupler Added | Coated Amount of Silver / Coated Amount of Coupler (mg/m² / mg/m²) | Remarks |
|---|---|---|---|---|---|
| 4 | [structure with CH₃OOC groups, NH, S-phenyl-CONHC₁₈H₃₇, trichlorophenyl] | Cp-D | 14.2 g | 165/532 | Comparison |
| 5 | [structure with Cl, C₁₃H₂₇CONH, NH, S-phenyl-C₁₂H₂₅, trichlorophenyl] | Cp-E | 14.5 g | 165/543 | Comparison |
| 6 | [structure with Cl, C₁₃H₂₇CONH, NH, S-phenyl-CONHC₁₈H₃₇, trichlorophenyl] | Cp-F | 16.3 g | 165/612 | Comparison |
| 7 | [structure with Cl, C₁₃H₂₇CONH, NH, S-phenyl-OC₁₂H₂₅, trichlorophenyl] | Cp-G | 14.8 g | 165/553 | Comparison |
| 8 | [structure with Cl, C₁₃H₂₇CONH, NH, S-(2-CH₃-4-OC₁₂H₂₅)phenyl, trichlorophenyl] | Cp-1 | 15.0 g | 165/561 | This Invention |
| 9 | [structure with Cl, C₁₃H₂₇CONH, NH, S-(2-OC₁₂H₂₅-5-Cl)phenyl, trichlorophenyl] | Cp-2 | 15.3 g | 165/574 | This Invention |

TABLE 1-continued

| Sample No. | Structure of Coupler | Coupler No. | Amount of Coupler Added | Coated Amount of Silver / Coated Amount of Coupler (mg/m² / mg/m²) | Remarks |
|---|---|---|---|---|---|
| 10 | (structure: pyrazolone with Cl, $C_{13}H_{27}CONH$-anilino, 2,4,6-trichlorophenyl-N, S-aryl with $OC_{12}H_{25}$ and $CH_3$) | Cp-3 | 15.0 g | 165/561 | This Invention |
| 11 | (structure: pyrazolone with Cl, $C_{13}H_{27}CONH$-anilino, 2,4,6-trichlorophenyl-N, S-aryl with $OC_4H_9$ and $C_8H_{17}(t)$) | Cp-6 | 14.8 g | 165/553 | This Invention |
| 12 | (structure: pyrazolone with Cl, $C_{13}H_{27}CONH$-anilino, 2,4,6-trichlorophenyl-N, S-aryl with $OC_8H_{17}$, $C_4H_9(t)$, $OC_8H_{17}$) | Cp-23 | 16.6 g | 165/620 | This Invention |
| 13 | (structure: pyrazolone with 2,4-dichloroanilino, 2,4,6-trichlorophenyl-N, S-aryl with $OC_4H_9$ and $C_8H_{17}(t)$) | Cp-25 | 11.6 g | 165/436 | This Invention |
| 14 | (structure: pyrazolone with Cl, succinimido-anilino, 2,4,6-trichlorophenyl-N, S-aryl with $OC_{12}H_{25}$ and $C_4H_9(t)$) | Cp-26 | 12.7 g | 165/474 | This Invention |

TABLE 2

| Sample No. | | Magenta Color Image $D_{max}$ | After Xenon Irradiation for 5 Days Magenta Density (Initial Density of 1.0) | Yellow Stain Density on white Background |
|---|---|---|---|---|
| 1 | Comparison | 2.10 | 0.75 | 0.35 |
| 2 | " | 1.74 | 0.17 | 0.41 |
| 3 | " | 2.02 | 0.23 | 0.52 |
| 4 | " | 1.98 | 0.22 | 0.39 |
| 5 | " | 2.23 | 0.35 | 0.36 |
| 6 | " | 1.98 | 0.21 | 0.36 |
| 7 | " | 2.31 | 0.43 | 0.48 |
| 8 | Present Invention | 2.29 | 0.76 | 0.31 |
| 9 | Present Invention | 2.30 | 0.78 | 0.30 |
| 10 | Present Invention | 2.25 | 0.86 | 0.29 |
| 11 | Present Invention | 2.28 | 0.88 | 0.29 |
| 12 | Present Invention | 2.21 | 0.91 | 0.30 |
| 13 | Present Invention | 2.09 | 0.77 | 0.26 |
| 14 | Present Invention | 2.11 | 0.81 | 0.26 |

As is apparent from Table 1 above, 2-equivalent couplers are used in Samples 2 to 14, although a 4-equivalent coupler is used in Sample 1. In order to confirm the reduction in the amount of silver halide used which is one object of the present invention, the coating amount of silver is reduced in Samples 2 to 14 to one half of that in Sample 1.

It is apparent from the results shown in Table 2 that the property of the releasing group of the coupler is largely influenced for obtaining the desired $D_{max}$ using only half amount of silver, and that the couplers according to the present invention have a high color forming property which can allow the possibility of reduction in the silver amount. On the other hand, it is very surprising that the light fastness of the magenta color images formed and the change of yellow density in white background depend largely on the structure of the releasing group among the couplers capable of reducing the amount of silver used. By this detailed investigation it has been found that releasing groups of an extremely restricted scope can achieve the objects of this invention.

EXAMPLE 2

On a paper support both surfaces of which were laminated with polyethylene were coated a first layer (undermost layer) to a sixth layer (uppermost layer) as shown in Table 3 in order to prepare a color photographic light-sensitive material which is designated Sample 15. A coating composition for a third layer was prepared in accordance with the procedure as described in Example 1. Thus samples were prepared using the couplers as shown in Table 4.

These samples were exposed using a sensitometer to light of 1,000 lux/sec equipped with a green filter, SP-2 (made by Fuji Photo Film Co., Ltd.). The, these samples were subjected to the same processing as described in Example 1. Then the samples were subjected to a fading test for 5 days using a Xenon fading tester (200,000 lux) in a manner analogous to Example 1. The results obtained are shown in Table 5 below.

TABLE 3

| | |
|---|---|
| Sixth Layer: (protective layer) | Gelatin (1,000 mg/m$^2$) |
| Fifth Layer: (red-sensitive layer) | Silver chlorobromide emulsion (Br: 50 mol %, silver: 300 mg/m$^2$), Gelatin (1,000 mg/m$^2$), Cyan coupler*[1] (400 mg/m$^2$), Coupler solvent*[2] (200 mg/m$^2$) |
| Fourth Layer: (interlayer) | Gelatin (1,200 mg/m$^2$), Ultraviolet light-absorbing agent*[3] (1,000 mg/m$^2$), Ultraviolet light-absorbing agent solvent*[2] (250 mg/m$^2$) |
| Third Layer: (green-sensitive layer) | Silver chlorobromide emulsion (Br: 50 mol %, silver: 330 mg/m$^2$), Gelatin (1,000 mg/m$^2$), Magenta coupler*[4] (375 mg/m$^2$), Coupler solvent*[5] (750 mg/m$^2$) |
| Second Layer: (interlayer) | Gelatin (1,000 mg/m$^2$) |
| First Layer: (blue-sensitive layer) | Silver chlorobromide emulsion (Br: 80 mol %, silver: 400 mg/m$^2$), Gelatin (1,200 mg/m$^2$), Yellow coupler*[6] (300 mg/m$^2$), Coupler solvent*[7] (150 mg/m$^2$) |
| Support: | Paper support both surfaces of which were laminated with polyethylene |

*[1]Coupler: 2-[α-(2,4-Di-tert-pentylphenoxy)butanamido]-4,6-dichloro-5-methylphenol
*[2]Solvent: Dibutyl phthalate
*[3]Ultraviolet light-absorbing agent: 2-(2-Hydroxy-3-sec-butyl-5-tert-butylphenyl)-benzotriazole
*[4]Coupler: 1-(2,4,6-Trichlorophenyl)-3-(2-chloro-5-tetradecanamido)anilino-2-pyrazolin-5-one (Cp-A)
*[5]Solvent: Tricresyl phosphate
*[6]Coupler: α-Pivaloyl-α-(2,4-dioxo-5,5'-dimethyl-oxazolidin-3-yl)-2-chloro-5-[α-(2,4-di-tert-pentylphenoxy)butanamido]acetanilide
*[7]Solvent: Dioctyl butyl phosphate

TABLE 4

| Sample No. | Coupler No. | Amount of Coupler Added (g) | Coated Amount of Silver/Coupler (mg/m$^2$/mg/m$^2$) | Remarks |
|---|---|---|---|---|
| 15 | Cp-A | 10.0 | 330/375 | Comparison |
| 16 | Cp-E | 14.5 | 165/543 | " |
| 17 | Cp-G | 14.8 | 165/553 | " |
| 18 | Cp-2 | 15.3 | 165/574 | Invention |
| 19 | Cp-6 | 14.8 | 165/553 | " |
| 20 | Cp-23 | 16.6 | 165/620 | " |

TABLE 5

| Sample No. | Xenon Irradiation for 5 Days Magenta Density (Initial Density of 2.0) | Yellow Stain Density in White Background | Remarks |
|---|---|---|---|
| 15 | 1.61 | 0.32 | Comparison |
| 16 | 0.73 | 0.33 | " |
| 17 | 0.86 | 0.45 | " |
| 18 | 1.70 | 0.29 | Invention |
| 19 | 1.80 | 0.27 | " |
| 20 | 1.85 | 0.27 | " |

It is apparent from the results shown in Table 5 above that the 2-equivalent magenta couplers according to the present invention can provide improved light fastness of color images, and also prevent the yellow discoloration of the white background due to light, by use together with a known magenta color image stabilizer.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon a photographic layer containing at least one coupler represented by formula (I) or (II)

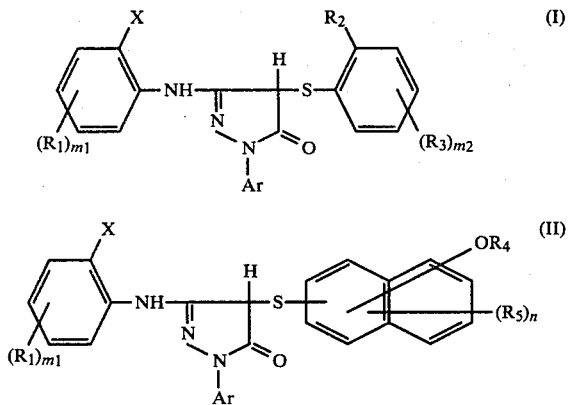

wherein Ar represents a phenyl group substituted with at least one substituent selected from the group consisting of a halogen atom, an alkyl group, an alkoxy group, an alkoxycarbonyl group, and a cyano group; X represents a halogen atom or an alkoxy group; $R_1$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group, or a trifluoromethyl group; $R_2$ represents a halogen atom, a hydroxy group, an alkyl group, an alkoxy group, or an aryl group; $R_3$ represents a hydrogen atom, a halogen atom, a hydroxy group, an alkyl group, an alkoxy group or an aryl group; at least one of $R_2$ and $R_3$ represents an alkoxy group; $m_1$ and $m_2$ each represents an integer from 1 to 4; $R_4$ represents an alkyl group or an aryl group; $R_5$ represents a hydrogen atom, a halogen atom, an alkyl group, an alkoxy group or an aryl group; n represents an integer from 1 to 6; and when $m_1$, $m_2$ and n each is 2 or more, each $R_1$, $R_3$ and $R_5$ may be the same or different.

2. A silver halide color photographic light-sensitive material as in claim 1, wherein the alkyl group for the substituent on the phenyl group represented by Ar is an alkyl group having from 1 to 22 carbon atoms.

3. A silver halide color photographic light-sensitive material as in claim 1, wherein the alkoxy group for the substituent on the phenyl group represented by Ar is an alkoxy group having from 1 to 22 carbon atoms.

4. A silver halide color photographic light-sensitive material as in claim 1, wherein the alkoxycarbonyl group for the substituent on the phenyl group represented by Ar is an alkoxycarbonyl group having from 2 to 23 carbon atoms.

5. A silver halide color photographic light-sensitive material as in claim 1, wherein the alkoxy group represented by X is an alkoxy group having from 1 to 22 carbon atoms.

6. A silver halide color photographic light-sensitive material as in claim 1, wherein the group $R_1$ includes an alkyl moiety having from 1 to 36 carbon atoms.

7. A silver halide color photographic light-sensitive material as in claim 1, wherein the group $R_1$ includes an aryl moiety having from 6 to 38 carbon atoms.

8. A silver halide color photographic light-sensitive material as in claim 1, wherein the alkyl group represented by $R_2$ is an alkyl group having from 1 to 22 carbon atoms.

9. A silver halide color photographic light-sensitive material as in claim 1, wherein the alkoxy group represented by $R_2$ is an alkoxy group having from 1 to 22 carbon atoms.

10. A silver halide color photographic light-sensitive material as in claim 1, wherein the alkyl group represented by $R_3$ is an alkyl group having from 1 to 22 carbon atoms.

11. A silver halide color photographic light-sensitive material as in claim 1, wherein the alkoxy group represented by $R_3$ is an alkoxy group having from 1 to 22 carbon atoms.

12. A silver halide color photographic light-sensitive material as in claim 1, wherein the alkyl group represented by $R_4$ is an alkyl group having from 1 to 22 carbon atoms.

13. A silver halide color photographic light-sensitive material as in claim 1, wherein the alkyl group represented by $R_5$ is an alkyl group having from 1 to 22 carbon atoms.

14. A silver halide color photographic light-sensitive material as in claim 1, wherein the alkoxy group represented by $R_5$ is an alkoxy group having from 1 to 22 carbon atoms.

15. A silver halide color photographic light-sensitive material as in claim 1, wherein the total number of carbon atoms included in the groups represented by $R_2$ and $R_3$ is at least 6.

16. A silver halide color photographic light-sensitive material as in claim 1, wherein the total number of carbon atoms included in the groups represented by $R_4$ and $R_5$ is at least 4.

17. A silver halide color photographic light-sensitive material as in claim 1, wherein the photographic layer is a light-sensitive silver halide emulsion layer.

18. A silver halide color photographic light-sensitive material as in claim 17, wherein the light-sensitive silver halide emulsion layer is a green-sensitive silver halide emulsion layer.

19. A silver halide color photographic light-sensitive material as in claim 18, wherein the photographic material further contains a blue-sensitive silver halide emulsion layer containing a yellow color-forming coupler and a red-sensitive silver halide emulsion layer containing a cyan color-forming coupler.

20. A silver halide color photographic light-sensitive material as in claim 19, wherein the yellow color-forming coupler and the cyan color-forming coupler are 2-equivalent couplers, respectively.

21. A silver halide color photographic light-sensitive material as in claim 1, wherein the coupler is a coupler represented by formula (I)

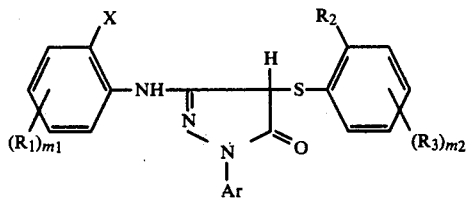

(I)

wherein Ar represents a phenyl group substituted with at least one substituent selected from the group consisting of a halogen atom, an alkyl group, an alkoxy group, an alkoxycarbonyl group and a cyano group; X represents a halogen atom or an alkoxy group; $R_1$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group or a trifluoromethyl group; $R_2$ represents a halogen atom, a hydroxy group, an alkyl group, an alkoxy group or an aryl group; $R_3$ represents a hydrogen atom, a halogen atom, a hydroxy group, an alkyl group, an alkoxy group or an aryl group; at least one of $R_2$ and $R_3$ represents an alkoxy group; $m_1$ and $m_2$ each represents an integer from 1 to 4; and when $m_1$ and $m_2$ each is 2 or more, each $R_1$ and $R_3$ may be the same or different.

22. A silver halide color photographic light-sensitive material as in claim 1, wherein the coupler of the formula (I) or (II) is coated in an amount of about $2 \times 10^{-3}$ mol to about $5 \times 10^{-1}$ mol per mol of silver.

* * * * *

REEXAMINATION CERTIFICATE (866th)
United States Patent [19]
Aoki et al.

[11] B1 4,351,897
[45] Certificate Issued Jun. 14, 1988

[54] COLOR PHOTOGRAPHIC LIGHT-SENSITIVE MATERIAL

[75] Inventors: Kozo Aoki; Nobuo Seto; Yoshiharu Yabuki; Masakazu Morigaki; Nobuo Furutachi; Kotaro Nakamura, all of Minami-ashigara, Japan

[73] Assignee: Fuji Photo Film Co., Ltd., Kanagawa, Japan

Reexamination Request:
No. 90/001,313, Aug. 24, 1987

Reexamination Certificate for:
Patent No.: 4,351,897
Issued: Sep. 28, 1982
Appl. No.: 291,886
Filed: Aug. 11, 1981

[30] Foreign Application Priority Data

Aug. 12, 1980 [JP] Japan .................. 55-110943

[51] Int. Cl.$^4$ .................. G03C 1/40; G03C 7/38
[52] U.S. Cl. .................. 430/555; 430/504; 430/505; 430/544; 430/551
[58] Field of Search .................. 430/555, 505, 544, 504, 430/551

[56] References Cited
U.S. PATENT DOCUMENTS
3,935,015  1/1976  Arai et al. .................. 96/74

Primary Examiner—Paul R. Michl

[57] ABSTRACT

A silver halide color photographic light-sensitive material is described comprising a support having thereon a photographic layer containing at least one coupler represented by formula (I) or (II)

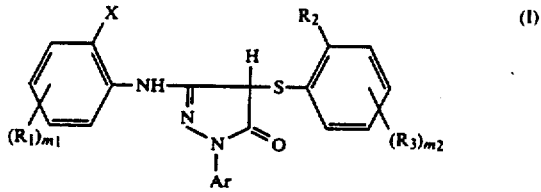

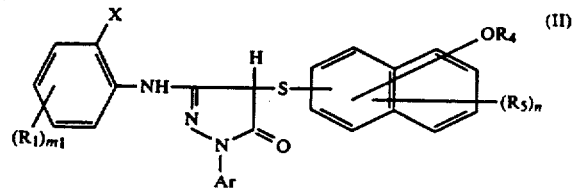

wherein Ar represents a phenyl group substituted with at least one substituent selected from a halogen atom, an alkyl group, an alkoxy group, an alkoxycarbonyl group and a cyano group; X represents a halogen atom or an alkoxy group; $R_1$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group, or a trifluoromethyl group; $R_2$ represents a halogen atom, a hydroxy group, an alkyl group, an alkoxy group or an aryl group; $R_3$ represents a hydrogen atom, a halogen atom, a hydroxy group, an alkyl group, an alkoxy group or an aryl group; at least one of $R_2$ and $R_3$ represents an alkoxy group; $m_1$ and $m_2$ each represents an integer from 1 to 4; $R_4$ represents an alkyl group or an aryl group; $R_5$ represents a hydrogen atom, a halogen atom, an alkyl group, an alkoxy group or an aryl group; n represents an integer from 1 to 6; and when $m_1$, $m_2$ and n each is 2 or more, each $R_1$, $R_3$ and $R_5$ may be the same or different.

The color photographic light-sensitive material containing a 2-equivalent magenta color image-forming coupler as described above has various advantages, for example, in that the dye formation efficiency in the color development step is high, the photographic properties are not influenced by variations in the pH of the color development bath, and the color images formed are fast to heat or light.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–22 is confirmed.

* * * * *